US006864384B2

(12) United States Patent
Brazdil et al.

(10) Patent No.: US 6,864,384 B2
(45) Date of Patent: Mar. 8, 2005

(54) PREPARATION OF VANADIUM ANTIMONY OXIDE BASED CATALYSTS USING NANO-SCALE IRON

(75) Inventors: James F. Brazdil, Glen Ellyn, IL (US); Joseph P. Bartek, Wheaton, IL (US); Steven S. Trail, St. Charles, IL (US)

(73) Assignee: The Standard Oil Company, Warrenville, IL (US)

( * ) Notice: Subject to any disclaimer, the term of this patent is extended or adjusted under 35 U.S.C. 154(b) by 191 days.

(21) Appl. No.: 10/306,017

(22) Filed: Nov. 27, 2002

(65) Prior Publication Data

US 2004/0102642 A1 May 27, 2004

(51) Int. Cl.[7] .................. C07C 253/18; B01J 23/745
(52) U.S. Cl. .................. 558/325; 502/338; 502/353; 502/305; 502/309; 502/310; 502/311; 502/312; 502/325; 502/324; 502/328; 502/330; 502/340; 502/344; 502/349; 502/352; 502/355
(58) Field of Search .................. 502/338, 353, 502/305, 309, 310, 311, 312, 325, 324, 328, 330, 355, 340, 349, 344, 352; 558/325

(56) References Cited

U.S. PATENT DOCUMENTS

| 3,681,421 | A | | 8/1972 | Barclay et al. ........... 160/465.3 |
| 3,860,534 | A | | 1/1975 | Harris et al. ................ 252/461 |
| 4,152,300 | A | * | 5/1979 | Riesser ....................... 502/302 |
| 4,746,641 | A | | 5/1988 | Guttmann et al. ........... 502/202 |
| 4,784,979 | A | | 11/1988 | Toft et al. ....................... 502/8 |
| 4,788,317 | A | | 11/1988 | Guttmann et al. ........... 558/319 |
| 4,879,264 | A | | 11/1989 | Toft et al. ....................... 502/8 |
| 5,008,427 | A | | 4/1991 | Brazdil, Jr. et al. ......... 558/319 |
| 5,094,989 | A | | 3/1992 | Lynch et al. ................ 502/202 |
| 5,214,016 | A | | 5/1993 | Brazdil et al. ............... 502/202 |
| 5,258,543 | A | | 11/1993 | Suresh et al. ................ 558/325 |
| 5,332,855 | A | | 7/1994 | Blanchard et al. .......... 558/319 |
| 5,432,141 | A | | 7/1995 | Brazdil, Jr. et al. ......... 502/311 |
| 5,498,588 | A | | 3/1996 | Brazdil et al. ............... 502/353 |
| 5,675,057 | A | | 10/1997 | Bremer et al. .............. 558/319 |
| 5,696,047 | A | | 12/1997 | Bremer et al. .............. 502/209 |
| 5,821,192 | A | | 10/1998 | Seely et al. ................. 502/353 |
| 5,866,502 | A | | 2/1999 | Cirjak et al. ................ 502/353 |
| 5,994,259 | A | | 11/1999 | Brazdil, Jr. et al. ......... 502/300 |
| 6,083,869 | A | | 7/2000 | Albonetti et al. ........... 502/325 |
| 6,087,524 | A | | 7/2000 | Brazdil, Jr. et al. ......... 558/320 |
| 6,156,920 | A | | 12/2000 | Brazdil, Jr. et al. ......... 558/319 |
| 2004/0102318 | A1 | * | 5/2004 | Brazdil et al. ............... 502/353 |
| 2004/0102319 | A1 | * | 5/2004 | Brazdil ....................... 502/353 |

FOREIGN PATENT DOCUMENTS

| EP | 0641771 A | 3/1995 |
| EP | 0767164 A | 4/1997 |
| EP | 0867221 A | 9/1998 |

* cited by examiner

*Primary Examiner*—Christina Johnson
(74) *Attorney, Agent, or Firm*—David P. Yusko

(57) ABSTRACT

A process for the manufacture of an improved iron promoted vanadium antimony oxide catalyst useful in the ammoxidation of propane to acrylonitrile wherein the source of iron (i.e. an iron containing compound such as $Fe_2O_3$) employed in the catalyst preparation has a BET surface area greater than 120 m$^2$/gram. Such catalysts are useful in processes for the ammoxidation of a $C_3$–$C_5$ paraffinic hydrocarbon to its corresponding α-β-unsaturated nitrile, the ammoxidation of propylene with $NH_3$ and oxygen to acrylonitrile, the ammoxidation of methylpyridine with $NH_3$ and oxygen to make cyanopyridine, the ammoxidation of m-xylene with $NH_3$ and oxygen to make isophthalonitrile, and the oxidation of o-xylene to make phthalic anhydride.

11 Claims, No Drawings

PREPARATION OF VANADIUM ANTIMONY OXIDE BASED CATALYSTS USING NANO-SCALE IRON

BACKGROUND OF THE INVENTION

1. Field of the Invention

The present invention is directed to iron promoted vanadium antimony oxide catalyst useful in the ammoxidation of a $C_3$–$C_5$ paraffinic hydrocarbon to its corresponding α-β-unsaturated nitrile ammoxidation of propylene with $NH_3$ and oxygen to acrylonitrile, ammoxidation of methylpyridine with $NH_3$ and oxygen to make cyanopyridine, the ammoxidation of m-xylene with $NH_3$ and oxygen to make isophthalonitrile and the oxidation of o-xylene to make phthalic anhydride. In particular, the present invention is directed to a process for the manufacture of an iron promoted vanadium antimony oxide catalyst useful in the ammoxidation of propane to acrylonitrile. More specifically, the instant invention relates to the preparation of an improved iron promoted vanadium antimony catalyst resulting from a catalyst preparation which utilizes a source of iron (i.e. an iron containing compound such as $Fe_2O_3$) having a BET surface area greater than about 120 m²/gram.

2. Description of the Prior Art

Commercial processes for the production of acrylonitrile employ propylene as a feedstock. However, because of the price differential between propylene and propane, an economic incentive exists for the development of a commercial process for the ammoxidation of propane to acrylonitrile. The development of such a process depends upon a viable catalyst useful for the conversion of propane to acrylonitrile.

Vanadium antimony type catalysts useful in the ammoxidation of propane to acrylonitrile along with various methods of making such catalysts are taught in the following U.S. Pat. Nos. 6,083,869; 5,994,259; 5,866,502; 5,498,588; 5,332,855; 5,258,543; 5,214,016; 5,008,427; 4,788,317; 4,784,979; 4,746,641; 3,860,534; and 3,681,421.

Many of these patents (e.g. U.S. Pat. Nos. 5;994,259; 5,498,588; 5,008,427) teach iron as an additional (sometimes optional) promoter for vanadium antimony type catalysts. The source of such iron was typically iron oxide ($Fe_2O_3$) which was obtained from commercial sources and consisted of large agglomerated particles of the iron oxide. Such compounds typically have a BET surface area of less than about 100 m²/gram.

SUMMARY OF THE INVENTION

The present invention is directed to a method for making an iron promoted vanadium antimony oxide catalyst having an atomic ratio of iron to vanadium greater than 0.2, wherein the source of iron used in the catalyst preparation is an iron containing compound having a BET surface area of greater than about 120 m²/gram.

An embodiment of present invention is an iron promoted vanadium antimony oxide catalyst comprising vanadium, antimony, iron, optionally at least one of tin and titanium, and optionally at least one promoter element selected from the group consisting of lithium, magnesium, sodium, calcium, strontium, barium, cobalt, chromium, gallium, nickel, zinc, germanium, niobium, zirconium, molybdenum, tungsten, copper, tellurium, tantalum, selenium, bismuth, cerium, indium, arsenic, boron, aluminum, and manganese, wherein the relative proportions of these elements are represented by the following general formula:

$V_aSb_bA_cFe_dD_eO_x$ wherein A when present is at least one of Sn and Ti

D when present is at least one of Li, Mg, Na, Ca, Sr, Ba, Co, Cr, Ga, Ni, Zn, Ge, Nb, Zr, Mo, W, Cu, Te, Ta, Se, Bi, Ce, In, As, B, Al, and Mn, and wherein a is 1, b is between about 0.5 to about 10, c is 0 to about 10, d is between 0.2 to about 10, e is 0 to about 10, and x is determined by the oxidation state of the cations present and wherein the source of iron used in the catalyst preparation is an iron containing compound having a BET surface area of greater than about 120 m²/gram.

Another embodiment of the present invention are catalytic processes for the ammoxidation of a $C_3$–$C_5$ paraffinic hydrocarbon to its corresponding α-β-unsaturated nitrile, the ammoxidation of propylene with $NH_3$ and oxygen to acrylonitrile, the ammoxidation of methylpyridine with $NH_3$ and oxygen to make cyanopyridine, the ammoxidation of m-xylene with $NH_3$ and oxygen to make isophthalonitrile, and the oxidation of o-xylene to make phthalic anhydride, wherein the catalyst employed in said processes are an iron promoted vanadium antimony oxide catalyst having an atomic ratio of iron to vanadium greater than 0.2 wherein the source of iron used in the preparation of the catalyst is an iron containing compound having a BET surface area of greater than about 120 m²/gram.

DETAILED DESCRIPTION OF THE INVENTION

The instant invention relates to a method for making an iron promoted vanadium antimony oxide catalyst having an atomic ratio of iron to vanadium greater than 0.2 wherein the source of iron employed in the catalyst preparation is an iron containing compound (e.g. $Fe_2O_3$) having a BET surface area of greater than about 120 m²/gram. The use of iron containing compounds having a BET surface area of greater than about 120 m²/gram is a highly effective source for iron promotion in vanadium antimonate based ammoxidation and oxidation catalysts. Iron promoted vanadium antimony oxide catalyst produced using such iron containing compounds having a BET surface area of greater than about 120 m²/gram exhibit superior activity and performance when compared to catalysts produced using other iron sources having BET surface areas less than about 100 m²/gram.

As used herein "BET surface area" refers to the Brunauer, Emmett and Teller (BET) method for surface area determination, which utilizes the isothermal adsorption of nitrogen to measure total surface area of a material. The BET surface area of the iron containing compound correlates with particle size distribution, i.e. iron containing compounds having a BET surface area of greater than about 120 m²/gram by predominantly small particles which are well dispersed and/or weakly agglomerated. In one embodiment, such compounds when observed at high magnification (×100,000) via SEM microscopy (FIG. 2) exhibit a majority of small particles less than about 20 nm. In another embodiment, such compounds when observed at high magnification (×100,000) via SEM microscopy (FIG. 3) exhibit a majority of small cylindrical particles less than about 40 nm×150 nm. In another embodiment, such compounds when observed at high magnification (×100,000) via SEM microscopy (FIG. 4) exhibit a majority of very small particles less than about 4 nm in diameter which are weakly agglomerated. As used herein "weakly agglomerated" means that the particles disassociate and disperse when such iron containing compounds are employed in the catalyst preparation described herein. Collectively, these various iron containing compounds having BET surface areas of greater than about 120 m²/gram are referred to herein as "nano-scale iron".

While not intending to be bound by theory, the addition of iron as a promoter yields a more active vanadium antimonate catalyst. However, excessive iron (or as now theorized, high localized iron concentrations) in a vanadium antimonate catalyst harms the selectivity of propane ammoxidation to acrylonitrile. For this reason, iron concentrations in prior art vanadium antimonate catalysts were generally kept low (i.e. the ratio of iron to vanadium not exceeding 0.2) to avoid harming selectivity. In contrast, the use of nano-scale iron allows for the incorporation of sufficient iron in a vanadium antimonate catalyst to give increased activity while not harming selectivity of propane ammoxidation to acrylonitrile. More specifically, nano-scale iron when incorporated in a vanadium antimonate catalyst remains dispersed in the catalyst crystal structure (as opposed to high localized iron concentrations) and yields a catalyst with increased activity. Since the iron remains dispersed more iron can be added to the catalyst to increase catalyst activity. In contrast, when an equivalent amount of iron is incorporated in such catalysts using an iron oxide having a BET surface area less than about 100 m²/gram as the source, the iron tends to agglomerate or cluster within the catalyst crystal structure producing a non homogeneous catalyst with large iron containing portions and both the activity and selectivity of the resulting catalysts are decreased.

The nano-scale iron containing compounds employed in the process claimed herein has a BET surface area of greater than about 120 m²/gram. In one embodiment, the BET surface area is greater than about 150 m²/gram. In another embodiment, the BET surface area is greater than about 200 m²/gram. In yet another embodiment, the BET surface area is greater than about 250 m²/gram. Furthermore, as described in earlier paragraphs, such nano-scale iron containing compounds predominantly comprise small particles that are well dispersed and/or only weakly agglomerated.

Typically, the iron containing compounds of used herein are or are derived from iron oxides, iron hydroxides and/or iron carbonates, and preferably an iron oxide. One source of nano-scale iron oxide is amorphous $Fe_2O_3$ made by combustion of iron pentacarbonyl. This material may be used as a dry or damp powder with moisture content between 0 and 30%, or as a slurry of the powder in water. The gamma form of $Fe_2O_3$ similar to the mineral maghemite may also be used. One source of iron hydroxides are iron (III) hydroxides or ferrihydrites made by precipitation of iron salts with a base. Additionally, ferrites, such as $MgFe_2O_4$, $ZnFe_2O_4$ or $BaFe_2O_4$ may be used to supply all or part of the iron, as long as they are in the proper size range. Mixed valence oxides such as magnetite, $Fe_3O_4$, or divalent oxides are also likely to be useful. The presence of carbonate may have some impact on viscosity of the catalyst precursor slurry during catalyst preparation. Iron containing compounds having BET surface areas greater than 120 m²/gram are commercially available.

Additionally, the spray dried micro-spheroidal iron promoted vanadium antimony oxide catalyst produced using nano-scale iron has good resistance to attrition when used in a fluidized bed catalytic reactor. Replacing the nano-scale iron with an iron salt, such as iron citrate, causes the catalyst precursor slurry to gel at much lower solids content, decreasing the resistance of the catalyst to attrition.

Catalyst Composition

Catalysts of the present invention comprise vanadium, antimony, iron, optionally at least one of tin and titanium, and optionally at least one promoter element selected from the group consisting of lithium, magnesium, sodium, calcium, strontium, barium, cobalt, chromium, gallium, nickel, zinc, germanium, niobium, zirconium, molybdenum, tungsten, copper, tellurium, tantalum, selenium, bismuth, cerium, indium, arsenic, boron, aluminum, and manganese, wherein the relative proportions of these elements are represented by the following general formula:

wherein A when present is at least one of Sn and Ti,
D when present is at least one of Li, Mg, Ca, Sr, Ba, Co, Fe, Cr, Ga, Ni, Zn, Ge, Nb, Zr, Mo, W, Cu, Te, Ta, Se, Bi, Ce, In, As, B, Al, and Mn,
and wherein a is 1, $0.5 \leq b \leq 10$, $0 \leq c \leq 10$, $0.2 < d \leq 10$, $0 \leq e \leq 10$, and x is determined by the oxidation state of the cations present. Preferably $0.25 < d \leq 10$. More preferably, $0.3 < d \leq 10$.

A preferred catalyst formulation, when applied to a process of manufacturing acrylonitrile or methacrylonitrile by catalytic reaction in the vapor phase of a paraffin selected from propane and isobutane with molecular oxygen and ammonia by catalytic contact of the reactants in a reaction zone, comprises vanadium, antimony, iron, molybdenum, arsenic, at least one of tin, titanium, chromium and gallium, and at least one other promoter element selected from the group consisting of lithium, magnesium, sodium, calcium, strontium, barium, cobalt, chromium, gallium, nickel, zinc, germanium, niobium, zirconium, molybdenum, tungsten, copper, tellurium, tantalum, selenium, bismuth, cerium, indium, arsenic, boron, aluminum, and manganese, wherein the relative proportions of these elements are represented by the following formula:

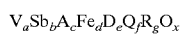

where
A is at least one of Ti, Sn, Cr, and Ga,
D is at least one of Li, Mg, Ca, Sr, Ba, Co, Ni, Zn, Ge, Nb, Zr, W, Cu, Te, Ta, Se, Bi, Ce, In, B, Al, and Mn,
Q is Mo,
R is As,
a is 1,
$0.8 \leq b \leq 4$,
$0.01 \leq c \leq 2$,
$0.2 < d \leq 2$,
$0 \leq e \leq 2$,
$0 < f < 0.01$ and more preferably $0 < f < 0.0045$,
$0 \leq g < 0.1$, and
x is determined by the oxidation state of the cations present.

In the above-described catalysts preferably "A" is Sn and Ti. Also, preferably $0.25 < d \leq 2$ and more preferably, $0.3 < d \leq 2$.

The above-described catalysts may be unsupported or supported on any suitable carrier. Examples of suitable carriers are silica, alumina, silica alumina, zirconia and the like.

Catalyst Preparation

The above-mentioned vanadium antimony oxide based catalysts can be prepared by any method known in the art. Typically, the production of the vanadium antimony oxide based catalysts described herein begins with the preparation of a catalyst precursor dispersion, solution, sol, or slurry (preferably but not exclusively and aqueous dispersion, solution, sol, or slurry) comprising vanadium, antimony and optionally other promoter elements, referred to herein as the "catalyst precursor slurry". Optionally, the slurry may be prepared using a liquid solvent medium which comprises an organic solvent, e.g. a liquid solvent comprising a mixture of water and an alcohol.

A particularly effective method of preparation of the catalyst precursor slurry is the so-called "peroxide method" disclosed in U.S. Pat. Nos. 4,784,979 and 4,879,264. Specifically according to U.S. Pat. No. 4,784,979, the a catalyst precursor slurry is prepared having vanadium and antimony in oxide form in the atomic ratio of Sb to V in the range from 0.8 to 4, usually from 1 to 3, by reacting the monoperoxovanadium ion, $VO(O_2)^+$, while in aqueous solution, with an antimony compound which contains Sb having a valence of 3, thereby reducing the average valence of the vanadium to less than 5 and oxidizing antimony to a valence state of 5. At least a portion of the $Sb^{+3}$ is so reduced, not necessarily all.

More specifically, the catalyst precursor slurry is prepared by reacting a vanadium compound with an aqueous hydrogen peroxide ($H_2O_2$) solution to form a dispersion containing the monoperoxovanadium ion, $VO(O_2)^+$, in solution, and reacting the latter with an antimony compound which contains Sb having a valence of 3, thereby reducing the average valence of the vanadium to less than 5 and oxidizing antimony to a valence state of 5, wherein the ratio of moles of $H_2O_2$ to atoms of V is at least 1. This ratio can be 1 or any amount over 1, but a ratio of 10 or less is usually sufficient.

The vanadium source (i.e. the vanadate, the vanadium compound, or the vanadium containing compound, as used herein) can be an inorganic or an organic compound of vanadium, but is usually an inorganic compound. The vanadium in the compound can have any initial valence. A partial list of such compounds includes any oxide of vanadium, such as $V_2O_5$, $V_7O_{13}$, VO, $VO_2$, $V_2O_3$, $V_3O_7$, etc.; any vanadium oxyhalide such as $VOCl_3$, $VOCl_2$, $(VO_2)Cl$, VOCl, VOBr, $VOBr_2$, $VOBr_3$; any vanadium halide such as $VF_3$, $VBr_3$, $VCl_2$, $VCl_3$, $VCl_4$, $VF_5$; vanadyl sulfate; metavanadic acid; pyro-vanadic acid; in short, any compound of vanadium that will react with an aqueous $H_2O_2$ solution.

The vanadium compound usually used in the reaction with $H_2O_2$ is one of the oxides. Because of availability and cost, $V_2O_5$ is often the compound that is chosen to react with the hydrogen peroxide.

The antimony source (i.e. the antimony compound or antimony containing compound, as used herein) chosen to react with the monoperoxovanadium ion in making the catalyst precursor of the invention can be an organic or an inorganic compound of antimony. A partial list of such compounds includes any of the following types of compounds containing antimony having a valence of 3: any such antimony oxide such as $Sb_2O_3$ and $Sb_2O_4$; SbOCl; any such antimony halide such as $SbBr_3$, $SbCl_3$, $SbF_3$ and $SbI_3$.

The antimony compound usually chosen to react with the peroxovanadium ion is one of the antimony oxides containing antimony having a valence of 3. Because of availability and cost $Sb_2O_3$ is ordinarily the chosen oxide. Of course, when the antimony compound is $Sb_2O_4$, the half of the Sb that is 5-valent is not useful to effect reduction of the 5-valent vanadium.

In the preparation of the catalyst precursor slurry, where the $H_2O_2$ reacts with the vanadium compound to produce the peroxovanadium ion, and the latter is thereafter reacted with the antimony compound, the vanadium compound can be contacted with the $H_2O_2$ before it is contacted with the antimony compound, and this has in practice usually been the procedure used. Alternatively, the antimony compound reactant can be present at the initial contact between the vanadium compound and $H_2O_2$, provided that both the V compound reaction with the $H_2O_2$ to form the monoperoxovanadium ion and the oxidation-reduction reaction of the latter with the Sb compound are faster than either the oxidation reaction of the $H_2O_2$ with the Sb compound or the vanadium compound-catalyzed decomposition of the $H_2O_2$. When the V compound is $V_2O_5$ and the Sb compound starting material is $Sb_2O_3$, this procedure can successfully be employed. Whether the antimony compound can be present at the initial contact between the V compound and the $H_2O_2$ can be determined by trial and error for other combinations of V and Sb substrates without undue experimentation.

An alternative method for the preparation of the catalyst precursor slurry is disclosed in U.S. Pat. No. 5,866,502. This method comprises heating an aqueous mixture comprising water soluble vanadates (e.g. $VO_4^{-3}$, $VO_3^{-1}$, $V_2O_5$) and $Sb_2O_3$ and, optionally, at least one compound comprising a promoter element to a temperature between 110° C. and 250° C. under autogenous pressure with agitation for a time sufficient to allow at least the slightly water soluble vanadates and $Sb_2O_3$ to react to form the catalyst precursor slurry. Suitable water-soluble vanadates and alternative antimony compounds for use in place of $Sb_2O_3$ are as described above for the "peroxide method".

For any preparation method, generally, compounds comprising promoter elements can be added at any time after the vanadium and antimony reaction has taken place. This includes the nano-iron compounds described herein as well as other compounds of element such as Ti, Sn, Fe, Cu, Mg, Mo, As, Li, Ca, Sr, Ba, Co, Ni, Zn, Ge, Nb, Zr, W, Te, Ta, Se, Bi, Ce, In, B, and Mn. Examples of sources of the metal promoters include nitrates, acetates, hydroxides, oxides, ammonium ion complexes, and carbonyls. Compounds of some elements such as Ti that form peroxo compounds can also be added before or with the addition of the $H_2O_2$ in the "peroxide method", but are usually most conveniently added after the vanadium and antimony compounds have reacted. The addition of promoter elements to the vanadium antimony oxide catalyst precursor can also be achieved by known methods in the art such as ion-exchange, solvo thermal treatment, and impregnation.

Alternatively, promoter elements may be added in sol form. For example, U.S. Pat. No. 6,087,524 discloses the preparation of tin promoted vanadium antimony oxide catalysts using tin sols (made from $SnO_2.xH2O$) wherein the tin sol was dispersed in a quaternary ammonium hydroxide. Additionally, a quaternary ammonium hydroxide (e.g. tetramethyl ammonium hydroxide, tetraethyl ammonium hydroxide) can be added to the catalyst slurry by itself in order to improve attrition resistance of the final catalyst. The quaternary ammonium hydroxide (QAH) is added such that the molar ratio of added QAH per gram of finished catalyst is between about 0.001 and about 10, preferably between about 0.005 and about 0.5.

The catalyst can be supported on any suitable carrier. Examples of such carriers are silica, alumina, silica-alumina, and the like. A particularly attrition resistant form of the catalyst contains silica, added as silica sol. Various types of silica sol, with particle sizes of about 5 to about 100 nanometers, can be used. The silica sol may be added to the catalyst precursor slurry at any time prior to drying the catalyst precursor slurry to form the catalyst precursor. Usually, these catalytic grade silica sols have low alkali metal content, and are stabilized by ammonia. Ion exchange with resins in acid or ammonium forms can also be used to remove excess alkali or alkaline earth ions from the silica.

After making the catalyst precursor slurry as described above the precursor slurry is dried to remove water and/or other solvents to yield a catalyst precursor which is then calcined to produce the finished catalyst. Optionally, the catalyst precursor slurry may first be concentrated by heating the catalyst precursor slurry in order to evaporate excessive residual quantities of water and/or other solvents. These heat treatments can be conducted as separate operations in multiple pieces of equipment or they can be conducted in single piece of equipment wherein the temperature is increased stepwise or continuously over time. In the preparation of a fixed bed catalyst, the catalyst precursor slurry is typically dried by heating at an elevated temperature and then shaped (e.g. extruded, pellitized, etc.) to the desired fixed bed catalyst size and configuration. In the preparation of fluid bed catalysts, the catalyst precursor slurry is typically spray dried to yield microspheroidal catalyst particles having particle diameters in the range from 10 to 200 microns.

After the catalyst is dried and shaped into its fixed or fluid bed form, the catalyst is subjected to a high temperature heat treatment or calcination in air or an oxygen enriched environment (i.e. a gaseous environment or atmosphere having a greater oxygen ($O_2$) content than air). The high temperature heat treatment or calcination is conducted at a temperature of at least 600° C., preferably above 750° C. For vanadium antimony oxide catalysts used for the ammoxidation of propane a high temperature heat treatment or calcination at a temperature of at least 780° C. is preferred. The high temperature heat treatment or calcination temperatures can be as high as 1200° C. Preferably the high temperature heat treatment or calcination is conducted at a temperature in the range of about 790° C. to about 1050° C. Optionally, as disclosed in U.S. Pat. Nos. 5,675,057 and 5,696,047, the catalyst may be further heat treated at an effective temperature that is at least 500° C. and at least 50° C. below said high temperature heat treatment calcination temperature.

The calcining step described above activates the catalyst to a significant degree, optionally the catalyst may be contacted with an alcohol (hydroxy compound) to further activate the catalyst. The catalyst can optionally be washed at any one or more points in the procedure using the methods disclosed in U.S. Pat. Nos. 3,860,534 and/or 5,094,989. Specifically, the catalyst can be washed after calcination by contacting said calcined catalyst with a hydroxy compound in liquid form (usually having no carbon-to-carbon unsaturation) selected from (1) cyclohexanol, (2) cyclopentanol, (3) a monohydroxy, acyclic hydrocarbon having 1–8 C atoms, usually 1–10 C atoms, and (4) a dihydroxy, acyclic hydrocarbon having 2–4 carbon atoms, and separating as a liquid said compound from said catalyst insofar as it is present beyond the amount wetting said catalyst, and thereafter drying said catalyst. Especially useful hydroxy compounds are the monohydroxy, acyclic hydrocarbons having 1 to 8 carbon atoms, and the dihydroxy, acyclic hydrocarbons having 2 to 4 carbon atoms. Most useful are the monohydroxy, acyclic hydrocarbons having 1 to 4 carbon atoms, especially isobutanol. The calcining step activates the catalyst to a significant degree, and the contacting with the alcohol (hydroxy compound) further activates the catalyst.

Processes

In another aspect of the present invention, there is provided a process for making an α,β unsaturated mononitrile selected from acrylonitrile and methacrylonitrile, by catalytic reaction in the vapor phase of a paraffin selected from propane and isobutane with molecular oxygen and ammonia and optionally a gaseous diluent, by catalytic contact of the foregoing reactants in a reaction zone with a catalyst, the feed to said reaction zone containing a mole ratio of said paraffin to $NH_3$ in the range of 2.5 to 16 and a mole ratio of said paraffin to $O_2$ in the range from 1 to 10, said catalyst having an empirical composition described above, said catalyst having been made by a method described above. The reaction temperature range can vary from 350° C. to 700° C. but is usually between 430° C. and 520° C. The average contact time can be from 0.01 to 10 seconds but is usually between 0.02 and 10 seconds and more preferably between 0.1 to 5 seconds. The pressure in the reaction zone is usually no more than 75 psia, but is preferably no more than 50 psia.

The catalyst may also be used in the ammoxidation of methylpyridine and m-xylene to cyanopyridine and isophthalonitrile or the oxidation of o-xylene to phthalic anhydride. The mole ratios of ammonia to methylpyridine and $O_2$ to methylpyridine are 1 to 5 and 1 to 10, respectively. The mole ratios of ammonia to m-xylene and $O_2$ to m-xylene are 1 to 5 and 1 to 10, respectively. In the phthalic anhydride reaction, the ratio of $O_2$ to o-xylene may range from 1 to 10.

The catalyst prepared by the process of the present invention may also be utilized in the ammoxidation of propylene or isobutene with ammonia and oxygen to produce acrylonitrile or methacrylonitrile. The mole ratio of ammonia to olefin may range from 1 to 5 and the mole ratio of $O_2$ to olefin may range from 1 to 10 in this reaction under conventional temperatures and conditions well known in the art.

The catalyst and processes described herein may be employed in any suitable reactor including fixed-bed, fluid-bed, and transport-bed reactors.

SPECIFIC EMBODIMENTS

For purposes of illustration only, the following examples are set forth to describe the catalyst and processes of the present invention. Surface area was measured by single point nitrogen gas adsorption using the BET method.

Part I. Preparation of Catalysts

EXAMPLE 1

Catalyst Composition: $V_1Sb_{1.6}Sn_{0.05}Ti_{0.05}Fe_{0.45}O_x$+20% $SiO_2$

Iron Description: super fine iron oxide

BET surface area: 250 m$^2$/gram

This catalyst was prepared by hydrothermal reaction in a 300 ml stirred Parr Autoclave with a 250 ml fused silica liner. First, 24 g water was added to the liner along with a temporary stir-bar. Then 30.8 g silica sol (32.5% $SiO_2$, low Na type), was added and stirred. A mixture of 3.89 g tin oxide sol (20.9% $SnO_2$) with 3.0 g 25% aqueous tetramethyl ammonium hydroxide (TMAOH) solution was added next. This tin oxide sol was prepared by heating $SnO_2$.xH2O with a solution of tetramethyl ammonium hydroxide (TMAOH) in water. The resultant translucent sol has 0.4 mole TMAOH per mole $SnO_2$. The super fine iron oxide powder (3.87 g), was added to that translucent white liquid, resulting in a chocolate brown slurry. Titanium oxide powder (0.43 g), $V_2O_5$ powder (9.79 g) and $Sb_2O_3$ powder (25.1 g) were then added in turn. All the raw materials were combined by stirring, after which the stir bar was removed. The expected yield of catalyst was 50 grams from the 189 g slurry, including water for rinsing. The full liner was placed in the autoclave vessel, and the lid with the stirrer attached. The reaction was conducted at 150° C. (63 PSIG autogenous pressure) for 4 hours after 1 hour heat-up. Stirring was continued for 1 hour while the autoclave cooled.

The slurry was transferred to a 400 ml beaker and stirred with heating to remove water until it became a thick paste with over 75% solids. The paste was dried in an oven at 120° C., then crushed and screened to yield between 20 and 35 Mesh particles. A portion of this precursor solid was pretreated in an oven at 325° C. for 3 hr to remove TMAOH. The pretreated material was calcined at 820° C. for 3 hours in air in a muffle furnace and post-calcined at 650° C. for 3 hours. The calcined material was washed with isobutanol, then dried at 120° C. before use.

EXAMPLE 2

Catalyst Composition $V_1Sb_{1.6}Sn_{0.05}Ti_{0.05}Fe_{0.45}O_x$+20% $SiO_2$

Iron Description: super fine iron oxide

BET surface area: 250 m$^2$/gram

This catalyst was prepared by hydrothermal reaction similarly to Example 1 but in a 450 ml stirred Parr Autoclave with a Pyrex glass liner. First, 30 g water was added to the liner along with a temporary stir-bar. Then 45.7 g silica sol (32.5% $SiO_2$, low Na type), was added and stirred. A mixture of 5.77 g tin oxide sol (20.9% $SnO_2$) with 4.5 g 25% aqueous TMAOH solution was added next. The super fine iron oxide powder (5.78 g), was added to that translucent white liquid, resulting in a chocolate brown slurry. Titanium oxide powder (0.64 g), $V_2O_5$ powder (14.55 g) and $Sb_2O_3$ powder (37.31 g) were then added in turn. All the raw materials were combined by stirring, after which the stir bar was removed. The expected yield of catalyst was 74 grams from the 262 g slurry, including water for rinsing. The full liner was placed in the autoclave vessel, and the lid with the stirrer attached. The reaction was conducted at 150° C. (63 PSIG autogenous pressure) for 4 hours after 1 hour heat-up. Stirring was continued for 1 hour while the autoclave cooled.

After the reaction, a few milliliters clear condensate was found between the liner and the autoclave vessel, but none of the slurry was lost. The slurry was transferred to a 400 ml beaker and stirred with heating to remove water until it became a thick paste with over 75% solids. The paste was dried in an oven at 120° C. and the resulting black solid was crushed smaller than 6 Mesh. This precursor solid was pretreated in an oven at 325° C. for 3 hr to remove TMAOH, then crushed and screened to yield between 20 and 35 Mesh particles. The pretreated material was calcined at 820° C. for 3 hours in air in a muffle furnace and post-calcined at 650° C. for 3 hours. The calcined material was washed with isobutanol, then dried at 120° C. before use.

EXAMPLE 3

Catalyst Composition: $V_1Sb_{1.6}Sn_{0.05}Ti_{0.05}Fe_{0.45}O_x$+20% $SiO_2$

Iron Description: super fine iron oxide

BET surface area: 250 m$^2$/gram

This catalyst was prepared by hydrothermal reaction in the same 450 ml Autoclave and according to the same recipe as Example 2. Somewhat less water was used for rinsing, since final slurry weight before reaction was 252 g. The direction of stirring was reversed, causing some of the paste to dry on the liner above the slurry, but none of the catalyst precursor was lost from the liner. After drying, the pretreatment and calcination were carried out in parallel with Example 2.

EXAMPLE 4

$V_1Sb_{1.5}Sn_{0.05}Ti_{0.05}Fe_{0.35}O_x$+20% $SiO_2$

Iron Description: super fine iron oxide

BET surface area: 250 m$^2$/gram

To make 0.3 moles of catalyst, $V_2O_5$ powder (27.29 g) was mixed with a solution consisting of 100 ml 30% $H_2O_2$ and 900 ml water in a two liter beaker. After reaction of the $V_2O_5$ was complete, $Sb_2O_3$ powder (65.59 g) was added followed by $TiO_2$ powder (1.20 g). The beaker was covered with a watch glass, and the mixture was stirred and heated for about 3.5 hours. Next, 10.83 g tin oxide sol (20.9% $SnO_2$) was added. This tin oxide sol was prepared by heating $SnO_2.xH2O$ with a solution of tetramethyl ammonium hydroxide (TMAOH) in water. The resultant translucent sol has 0.4 mole TMAOH per mole $SnO_2$. The super fine iron oxide powder (8.38 g), was added after mixing the tin sol with the slurry. Silica was added last as a 32.5% silica sol, with 81.0 g giving 20% wt $SiO_2$ in finished catalyst. The complete slurry was stirred with heating to remove water until it became a stiff paste near 30% solids. The paste was dried in an oven at 120° C., then crushed to particles smaller than 6 Mesh. Nearly all the precursor solid was pretreated in an oven at 325° C. for 3 hr to remove TMAOH. The resulting solid was crushed and screened to give 20/35 Mesh particles. A portion of the pretreated material was calcined at 820° C. for 3 hours in air in a muffle furnace and post-calcined at 650° C. for 3 hours. The calcined material was washed with isobutanol, then dried at 120° C. before use.

EXAMPLE 5

$V_1Sb_{1.5}Sn_{0.2}Ti_{0.05}Fe_{0.35}O_x$+20% $SiO_2$

Iron Description: super fine iron oxide

BET surface area: 250 m$^2$/gram

This catalyst was prepared similarly to that in Example 4. The amount of tin oxide sol added was adjusted to 43.3 g in accordance with the final composition given above.

EXAMPLE 6

$V_1Sb_{1.5}Sn_{0.2}Ti_{0.15}Fe_{0.35}O_x$+20% $SiO_2$

Iron Description: super fine iron oxide

BET surface area: 250 m$^2$/gram

This catalyst was prepared similarly to that in Example 4. The amount of tin oxide sol added was adjusted to 43.3 g, and the amount of $TiO_2$ powder was adjusted to 3.6 g in accordance with the final composition given above.

EXAMPLE 7

$V_1Sb_{1.5}Sn_{0.35}Ti_{0.10}Fe_{0.35}O_x$+20% $SiO_2$

Iron Description: super fine iron oxide

BET surface area: 250 m$^2$/gram

This catalyst was prepared similarly to that in Example 4. The amount of tin oxide sol added was adjusted to 75.7 g, and the amount of $TiO_2$ powder was adjusted to 2.4 g in accordance with the final composition given above.

EXAMPLE 8

$V_1Sb_{1.6}Sn_{0.05}Ti_{0.05}Fe_{0.45}O_x$+20% $SiO_2$

Iron Description: Yellow Iron Oxide (HPX 6232 from Elementis plc)

BET surface area: 160 m$^2$/gram

This catalyst was prepared similarly to the catalyst used in Example 1 of this invention. The Yellow Iron Oxide powder (HPX 6232 from Elementis plc) had a surface area by the B.E.T. method of 160 sq m/g after drying 1 hour at 300° C., whereupon the powder became dark red and lost 15% weight. The weight loss on drying and the X-ray diffraction pattern for the un-dried powder both indicate that Goethite, FeO(OH), was the principal crystalline phase. The yellow-orange iron oxide powder (4.66 g) was combined with the rest of the ingredients to yield 50 g catalyst and water to make 164.8 g light tan slurry in a 250 ml fused silica liner. After reaction in the Autoclave as in Example 1, the slurry was dried to a thick paste with 63% solids. Further processing to make a finished catalyst was the same as in Example 1.

EXAMPLE 9

$V_1Sb_{1.6}Sn_{0.05}Ti_{0.05}Fe_{0.45}O_x$+20% $SiO_2$

Iron Description: Fe(OH)$_3$ Slurry in H$_2$O

BET surface area: 137 m$^2$/gram

This catalyst was prepared in a 300 ml stirred Parr Autoclave similarly to the catalyst used in Example 1 of this invention. The iron was added as 39 g of a water slurry of Fe(OH)$_3$ which contained 3.9 g Fe$_2$O$_3$. When this slurry was dried to 300° C. (1 hr) its solids content was found to be 9.94%, and the surface area of the resulting brown gel was 137 sq. m/g. After it was added to the fused silica liner, the other liquids and solids were added to make 180 g total slurry. After reaction in the Autoclave as in Example 1, the slurry was dried to a thick paste with 74% solids. Further processing to make a finished catalyst was the same as in Example 1.

COMPARATIVE EXAMPLE A

Catalyst Composition: $V_1Sb_{1.6}Sn_{0.05}Ti_{0.05}Fe_{0.45}O_x$+20% $SiO_2$

Iron Description: Nano Tek® FeO$_x$ Powder

BET surface area: 44 m$^2$/gram

This catalyst was prepared in the same 450 ml Autoclave as Examples 2 and 3, using the same recipe to make 74 g catalyst. The iron source (5.75 g) was Nano Tek® iron oxide powder with typical average particle size of 26 nanometers from Nanophase Technologies Corp. Its bulk density was 0.15 g/ml, indicating that it was dispersed rather than agglomerated. Final weight of slurry was 275 g before reaction. The remaining steps in the catalyst preparation were carried out as for is Example 3.

COMPARATIVE EXAMPLE B

Catalyst Composition: $V_1Sb_{1.6}Sn_{0.05}Ti_{0.05}Fe_{0.45}O_x$+20% $SiO_2$

Iron Description: Red Iron Oxide (HPX 6231 from Elementis plc)

BET surface area: 101 m$^2$/gram

This catalyst was prepared similarly to the catalyst used in Example 1 of this invention. The Red Iron Oxide powder (HPX 6231 from Elementis plc) had a surface area by the B.E.T. method of 101 sq m/g. It was prepared by heating ferrous sulfate crystals and each agglomerate is a porous replica of the initial crystal. The red-orange iron oxide powder (3.87 g) was combined with the rest of the ingredients to yield 50 g catalyst and water to make 168.5 g pink slurry in a 250 ml fused silica liner. The liner was inserted in the 300 ml autoclave vessel and the stirred slurry was heated for four hours at 150° C. after one hour heat-up. All solids were retained in the liner. The slurry was dried as for Example 1, giving a dark chocolate colored paste which dried further to a dark colored solid with some red mottling. Further steps in the catalyst preparation were carried out as for Example 1.

COMPARATIVE EXAMPLE C

Catalyst Composition $V_1Sb_{1.5}Sn_{0.05}Ti_{0.05}Fe_{0.35}O_x$+20% $SiO_2$

Iron Description: Precipitated Iron Oxide Powder (Bayoxide® 1352)

BET surface area: 4 to 5 m$^2$/gram

This catalyst was prepared similarly to Catalysts 4–7 of the invention. To make 0.3 mole catalyst, V$_2$O$_5$ powder (27.29 g) was mixed with a solution consisting of 100 ml 30% H$_2$O$_2$ and 900 ml water in a two liter beaker. After reaction of the V$_2$O$_5$ was complete, Sb$_2$O$_3$ (65.59 g) was added, followed by TiO$_2$ powder (1.20 g ). The beaker was covered with a watch glass, and the mixture was stirred and heated for about 2.3 hours. Next, 10.82 g tin oxide sol (20.9% SnO$_2$) was added. This tin oxide sol was prepared by heating SnO$_2$.xH2O with a solution of tetramethyl ammonium hydroxide (TMAOH) in water. The resultant translucent sol has 0.4 mole TMAOH per mole SnO$_2$. The precipitated iron oxide powder (Bayoxide® 1352, 8.38 g) was mixed with water and added after mixing the tin sol with the slurry. According to Bayer, this material is near 0.3 micron (300 nm) in diameter, consistent with its surface area of 4–5 sq. m/g. It also has low porosity according to A. W. M. de Laat and H. F. M. Schoo, J. Colloid and Interface Sci. 191, 416 (1997), who made a more complete analysis of the nitrogen adsorption isotherm for similar powder from Bayer. Silica was added last as a 32.5% silica sol (low Na type), with 81.0 g giving 20% wt SiO$_2$ in finished catalyst. The complete slurry was stirred with heating to remove water until it became a stiff paste near 32% solids. The paste was dried in an oven at 120° C., then crushed to particles smaller than 6 Mesh. Nearly all of the precursor solid was pretreated in an oven at 325° C. for 3 hr to remove TMAOH. The resulting dark chocolate brown solid was crushed and screened to give between 20 and 35 Mesh particles. A portion of the pretreated material was calcined at 820° C. for 3 hours in air in a muffle furnace and post-calcined at 650° C. for 3 hours. The calcined material was washed with isobutanol, then dried at 120° C. before use.

COMPARATIVE EXAMPLE D

Catalyst Composition: $V_1Sb_{1.6}Sn_{0.05}Ti_{0.05}Fe_{0.45}O_x$+20% $SiO_2$

Iron Description: dried precipitated iron hydroxide

BET surface area: 59 m$^2$/gram

The catalyst was prepared similarly to Example 4. The dried precipitated iron hydroxide powder (14.5 g) was added to the slurry after the tin oxide sol. The dark red-brown iron hydroxide powder contained 75% Fe$_2$O$_3$ as received. After drying at 325° C. (2 hr), its surface area was 59 sq. m/g Next, the silica sol (85.8 g) with 32.5% SiO$_2$ was added before stirring the slurry with heating until it became a thick paste once the solids content reached 30%. Further steps in the catalyst preparation were carried out as for Example 4.

Part II Catalyst Testing

The catalysts prepared in Part I above were tested in a fixed-bed micro-reactor made of 0.25 inch O.D. titanium tubing immersed in a temperature controlled molten salt bath. The molar ratios of the feed compositions, reaction temperatures and contact times for the tests are listed in Table 2 below. All tests were conducted at a reactor temperature and pressure of 480° C. and 15 psig. Product analysis was done with two gas chromatographs. One was fitted with a packed Carbowax on Carbopak column to determine nitrites in liquids collected in an ice-cooled oxalic acid scrubber. The other was fitted with molecular sieve and silicone oil columns for analysis of fixed gases and light hydrocarbons in the feed and effluent gas streams. Ammonia and HCN were determined by titration.

TABLE 1

| Example No. | Composition | Iron oxide BET Surface Area ($m^2/g$) |
|---|---|---|
| 1 | $V_1Sb_{1.6}Sn_{0.05}Ti_{0.05}Fe_{0.45}O_x$ + 20% $SiO_2$ | 250 |
| 2 | $V_1Sb_{1.6}Sn_{0.05}Ti_{0.05}Fe_{0.45}O_x$ + 20% $SiO_2$ | 250 |
| 3 | $V_1Sb_{1.6}Sn_{0.05}Ti_{0.05}Fe_{0.45}O_x$ + 20% $SiO_2$ | 250 |
| 4 | $V_1Sb_{1.5}Sn_{0.05}Ti_{0.05}Fe_{0.35}O_x$ + 20% $SiO_2$ | 250 |
| 5 | $V_1Sb_{1.5}Sn_{0.2}Ti_{0.05}Fe_{0.35}O_x$ + 20% $SiO_2$ | 250 |
| 6 | $V_1Sb_{1.5}Sn_{0.2}Ti_{0.15}Fe_{0.35}O_x$ + 20% $SiO_2$ | 250 |
| 7 | $V_1Sb_{1.5}Sn_{0.35}Ti_{0.10}Fe_{0.35}O_x$ + 20% $SiO_2$ | 250 |
| 8 | $V_1Sb_{1.6}Sn_{0.05}Ti_{0.05}Fe_{0.45}O_x$ + 20% $SiO_2$ | 160 |
| 9 | $V_1Sb_{1.6}Sn_{0.05}Ti_{0.05}Fe_{0.45}O_x$ + 20% $SiO_2$ | 137 |
| A | $V_1Sb_{1.6}Sn_{0.05}Ti_{0.05}Fe_{0.45}O_x$ + 20% $SiO_2$ | 44 |
| B | $V_1Sb_{1.6}Sn_{0.05}Ti_{0.05}Fe_{0.45}O_x$ + 20% $SiO_2$ | 101 |
| C | $V_1Sb_{1.5}Sn_{0.05}Ti_{0.05}Fe_{0.35}O_x$ + 20% $SiO_2$ | 4–5 |
| D | $V_1Sb_{1.6}Sn_{0.05}Ti_{0.05}Fe_{0.45}O_x$ + 20% $SiO_2$ | 59 |

TABLE 2

| Example | Reactor Feed Mixture C3H8/NH3/O2/N2 | Contact Time (sec) | Propane Conversion | Acrylonitrile Selectivity | Acrylonitrile Productivity |
|---|---|---|---|---|---|
| 1 | 3.0/0.81/2.0/2.0 | 0.87 | 19.4% | 56.3% | 0.211 |
| 2 | 3.0/0.89/2.1/2.1 | 0.78 | 19.52% | 55.45% | 0.227 |
| 3 | 3.0/0.88/2.1/2.0 | 0.81 | 20.27% | 53.63% | 0.224 |
| 4 | 3.0/0.81/2.0/2.0 | 1.69 | 20.3% | 59.1% | 0.119 |
| 5 | 3.0/0.82/2.0/2.0 | 1.12 | 20.96% | 55.35% | 0.182 |
| 6 | 3.0/0.82/2.0/2.0 | 0.92 | 18.4% | 55.6% | 0.192 |
| 7 | 3.0/0.79/2.0/2.0 | 0.77 | 19.96% | 55.58% | 0.229 |
| 8 | 3.0/0.81/1.98/1.99 | 1.00 | 20.0% | 54.7% | 0.232 |
| 9 | 3.0/0.81/1.99/2.01 | 0.73 | 19.4% | 56.3% | 0.258 |
| A | 3.0/0.84/2.0/2.0 | 1.94 | 18.9% | 55.8% | 0.090 |
| B | 3.0/0.80/2.0/2.0 | 2.93 | 18.8% | 50.9% | 0.050 |
| C | 3.0/0.79/2.0/2.0 | 2.39 | 19.6% | 54.9% | 0.079 |
| D | 3.0/0.78/2.0/2.0 | 2.24 | 19.06% | 52.9% | 0.087 |

Notes:
1. Contact time is the number of seconds elapsed prior to achieving approximately 19–20% propane conversion.
2. Acrylonitrile Selectivity is the ratio of moles of acrylonitrile produced to moles of propane converted expressed in percent.
3. Acrylonitrile Productivity is the weight of acrylonitrile produced per unit weight of catalyst per hour (wt AN/wt catalyst/hr).

Iron promoted vanadium antimony oxide catalyst made with nano-scale iron oxide having a BET surface area greater than 120 $m^2/g$ are shown in Examples 1 to 9. Similar iron promoted vanadium antimony oxide catalysts made with iron oxide having a BET surface area less than 120 $m^2/g$ are shown in Comparative Examples A, B, C and D. Table 2 illustrates that the most active catalysts, i.e. those requiring the shortest contact time to reach 19–20% propane conversion, were Examples 1, 2, 3, 7 and 9 of the Invention. Their selectivities to acrylonitrile were also good. Acrylonitrile selectivity is the highest for propane ammoxidation over the catalyst of Example 4, which is not quite as active as the catalysts of Examples 1, 2 and 3. The catalysts of Examples 5, 6 and 7 made using the same procedure as Example 4 are more active but not quite as selective as Example 4. While the Acrylonitrile Productivity of Example 4 is not as high as that of the catalysts of Examples 1, 2 and 3, it is higher than that of Comparative Examples A, B, C and D.

While the catalysts of Examples 8 and 9 are not made from an iron oxide having a BET surface area as large as the iron oxide used in Examples 1–7, their activity and selectivity are very near those of catalysts from Examples 1, 2 and 3 made the same way. Field Emission Scanning Electron Microscope (SEM) photographs (×100,000 magnification) of the iron sources employed for Examples 1 through 9 reveal that the iron sources in Examples 8 and 9 have a different distribution of particles sizes and shapes as compared to the iron source employed for Examples 1–7, yet the SEM photographs also reveal that these sources share in common a majority of smaller size particles (as compared to the iron sources used in Comparative Examples A, B, C and D) which are well dispersed and/or weakly agglomerated.

Comparative Examples A, B, C and D all had BET surface areas of less than 120 m2/g. SEM photographs (×100,000 magnification) of the iron sources employed in Examples A and B revealed that the iron sources employed in Examples A and B typically comprised a majority of larger particles or firmly agglomerated particles. Comparative Example A (which exhibited larger particles in the SEM photographs) is much less active than the catalysts of Examples 1, 2 and 3 made similarly and with the same composition. The iron oxide particles of Comparative Example B were agglomerated and not well dispersed in the SEM photographs and had a BET surface area of 101 $m^2/g$. The catalyst of Comparative Example B was less active and had lower selectivity than the catalysts of Examples 1 to 7 made with dispersed nano-scale iron oxide having a larger BET surface area.

Comparative Example C (BET surface area of 4–5 $m^2/g$) has the same composition as Example 4 (BET surface area of 250 $m^2/g$) and was made similarly, but was less active and selective than Example 4.

As can be seen from Table 2 the combination of low activity and selectivity results in low acrylonitrile productivity as well.

It is to be understood that the subject invention is not to be limited by the exact description set forth in the examples herein. These have been provided merely to demonstrate the operability of the invention herein described. The selection of catalysts, metal sources, supports, concentrations, contact times, solids loadings, feedstocks, reaction conditions, and products can be determined from the total specification disclosure herein disclosed and described, without departing from the spirit of the invention and the scope of the invention, including modifications and variations, that fall within the boundaries of the attached claims.

That which is claimed is:

1. A method for making an iron promoted vanadium antimony oxide catalyst having an atomic ratio of iron to vanadium greater than 0.2, comprising preparing a slurry comprising vanadium, antimony, and iron, wherein the source of iron used in the catalyst preparation is an iron containing compound having a BET surface area greater than 120 $m^2$/gram.

2. The method of claim 1 wherein the iron containing compound has a BET surface area greater than 150 $m^2$/gram.

3. The method of claim 1 wherein the iron containing compound has a BET surface area greater than 200 $m^2$/gram.

4. The method of claim 1 wherein the iron containing compound is selected from the group consisting of iron oxide, iron hydroxides, iron carbonates and mixtures thereof.

5. The method of claim 1 wherein the iron promoted vanadium antimony oxide catalyst comprises vanadium, antimony, iron, optionally at least one of tin and titanium, and optionally at least one promoter element selected from the group consisting of lithium, magnesium, sodium, calcium, strontium, barium, cobalt, chromium, gallium, nickel, zinc, germanium, niobium, zirconium, molybdenum, tungsten, copper, tellurium, tantalum, selenium, bismuth, cerium, indium, arsenic, boron, aluminum, and manganese, wherein the relative proportions of these elements are represented by the following general formula:

$$V_aSb_bA_cFe_dD_eO_x$$

wherein A when present is at least one of Sn and Ti

D when present is at least one of Li, Mg, Ca, Sr, Ba, Co, Cr, Ga, Ni, Zn, Ge, Nb, Zr, Mo, W, Cu, Te, Ta, Se, Bi, Ce, In, As, B, Al, and Mn, and wherein a is 1, $0.5 \leq b \leq 10$, $0 \leq c < 10$, $0.2 < d \leq 10$, $0 \leq e \leq 10$, and x is determined by the oxidation state of the cations present.

6. The method of claim 1 wherein the iron promoted vanadium antimony oxide catalyst comprises vanadium, antimony, iron, molybdenum, arsenic, at least one of tin, titanium, chromium and gallium, and at least one other promoter element selected from the group consisting of lithium, magnesium, sodium, calcium, strontium, barium, cobalt, chromium, gallium, nickel, zinc, germanium, niobium, zirconium, molybdenum, tungsten, copper, tellurium, tantalum, selenium, bismuth, cerium, indium, arsenic, boron, aluminum, and manganese, wherein the relative proportions of these elements are represented by the following formula:

$$V_aSb_bA_cFe_dD_eQ_fR_gO_x$$

where

A is at least one of Ti, Sn, Cr, and Ga

D is at least one of Li, Mg, Ca, Sr, Ba, Co, Ni, Zn, Ge, Nb, Zr, W, Cu, Te, Ta, Se, Bi, Ce, In, B, Al and Mn Q is Mo R is As a is 1

$0.8 \leq b \leq 4$ $0.01 \leq c \leq 2$ $0.2 < d \leq 2$ $0 \leq e \leq 0.01$ $0 < f < 0.1$ $0 \leq g < 0.1$ x is determined by the oxidation state of the cations present.

7. The method of claim 3, wherein $0 < f < 0.0045$.

8. An iron promoted vanadium antimony oxide catalyst comprising vanadium, antimony, iron, optionally at least one of tin and titanium, and optionally at least one promoter element selected from the group consisting of lithium, magnesium, sodium, calcium, strontium, barium, cobalt, chromium, gallium, nickel, zinc, germanium, niobium, zirconium, molybdenum, tungsten, copper, tellurium, tantalum, selenium, bismuth, cerium, indium, arsenic, boron, aluminum, and manganese, wherein the relative proportions of these elements are represented by the following general formula:

$$V_aSb_bA_cFe_dD_eO_x$$

wherein A when present is at least one of Sn and Ti

D when present is at least one of Li, Mg, Ca, Sr, Ba, Co, Cr, Ga, Ni, Zn, Ge, Nb, Zr, Mo, W, Cu, Te, Ta, Se, Bi, Ce, In, As, B, Al, and Mn, and wherein a is 1, $0.5 \leq b \leq 10$, $0 \leq c \leq 10$, $0.2 < d \leq 10$, $0 \leq e \leq 10$, and x is determined by the oxidation state of the cations present and wherein the source of iron used in the catalyst preparation is an iron containing compound having a BET surface area greater than 120 m²/gram.

9. An iron promoted vanadium antimony oxide catalyst comprising vanadium, antimony, iron, molybdenum, arsenic, at least one of tin, titanium, chromium and gallium, and at least one other promoter element selected from the list consisting of lithium, magnesium, sodium, calcium, strontium, barium, cobalt, chromium, gallium, nickel, zinc, germanium, niobium, zirconium, molybdenum, tungsten, copper, tellurium, tantalum, selenium, bismuth, cerium, indium, arsenic, boron, aluminum, and manganese, wherein the relative proportions of these elements are represented by the following formula:

$$V_aSb_bA_cFe_dD_eQ_fR_gO_x$$

where

A is at least one of Ti, Sn, Cr, and Ga

D is at least one of Li, Mg, Ca, Sr, Ba, Co, Ni, Zn, Ge, Nb, Zr, W, Cu, Te, Ta, Se, Bi, Ce, In, B, Al, and Mn Q is Mo R is As a is 1

$0.8 \leq b \leq 4$ $0.01 \leq c \leq 2$ $0.2 < d \leq 2$ $0 \leq e \leq 2$ $0 < f < 0.01$ $0 \leq g < 0.1$ x is determined by the oxidation state of the cations present, and wherein the source of iron used in the catalyst preparation is an iron containing compound having a BET surface area greater than 120 m²/gram.

10. The catalyst of claim 9, wherein $0 < f < 0.0045$.

11. A process of manufacturing at least one of acrylonitrile and methacrylonitrile by catalytic reaction in the vapor phase of a paraffin selected from propane and isobutane with molecular oxygen and ammonia by catalytic contact of the reactants in a reaction zone, where in the catalyst comprises vanadium, antimony, iron, molybdenum, arsenic, at least one of tin, titanium, chromium and gallium, and at least one other promoter element selected from the group consisting of lithium, magnesium, sodium, calcium, strontium, barium, cobalt, chromium, gallium, nickel, zinc, germanium, niobium, zirconium, molybdenum, tungsten, copper, tellurium, tantalum, selenium, bismuth, cerium, indium, arsenic, boron, aluminum, and manganese, wherein the relative proportions of these elements are represented by the following formula:

$$V_aSb_bA_cFe_dD_eQ_fR_gO_x$$

where

A is at least one of Ti, Sn, Cr, and Ga

D is at least one of Li, Mg, Ca, Sr, Ba, Co, Ni, Zn, Ge, Nb, Zr, W, Cu, Te, Ta, Se, Bi, Ce, In, B, Al, and Mn Q is Mo R is As a is 1

$0.8 \leq b \leq 4$ $0.01 \leq c \leq 2$ $0.01 \leq d \leq 2$ $0 \leq e \leq 2$ $0 < f < 0.01$ and more preferably $0 < f < 0.0045$ $0 \leq g < 0.1$ x is determined by the oxidation state of the cations present, and wherein the source of iron used in the catalyst preparation is an iron containing compound having a BET surface area greater than 120 $m^2$/gram.

* * * * *